US008518019B2

(12) United States Patent
Green

(10) Patent No.: US 8,518,019 B2
(45) Date of Patent: Aug. 27, 2013

(54) VALVE ASSEMBLY INCLUDING A DISSOLVABLE VALVE MEMBER

(75) Inventor: Kurt E. Green, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 709 days.

(21) Appl. No.: 12/485,205

(22) Filed: Jun. 16, 2009

(65) Prior Publication Data

US 2009/0326483 A1    Dec. 31, 2009

Related U.S. Application Data

(60) Provisional application No. 61/076,850, filed on Jun. 30, 2008.

(51) Int. Cl.
*A61M 27/00* (2006.01)
*A61M 25/00* (2006.01)
*A61M 25/14* (2006.01)
*A61M 39/22* (2006.01)

(52) U.S. Cl.
USPC ...... 604/544; 604/540; 604/167.03; 604/247; 604/318; 604/319; 604/327

(58) Field of Classification Search
USPC ............ 604/415, 408, 405, 403, 327, 319, 604/318, 540, 288.03, 288, 247, 238, 237, 604/236, 167.03, 92
See application file for complete search history.

(56) References Cited

U.S. PATENT DOCUMENTS

| | | | | |
|---|---|---|---|---|
| 3,511,254 A | * | 5/1970 | Dyer et al. | 137/67 |
| 3,586,018 A | | 6/1971 | Bogardh et al. | |
| 3,848,603 A | * | 11/1974 | Throner | 604/540 |
| 4,601,880 A | * | 7/1986 | Wong et al. | 422/28 |
| 4,693,712 A | * | 9/1987 | Bates | 604/323 |
| 5,049,139 A | * | 9/1991 | Gilchrist | 604/265 |
| 5,122,118 A | | 6/1992 | Haber et al. | |
| 5,201,724 A | * | 4/1993 | Hukins et al. | 604/265 |
| 5,470,585 A | * | 11/1995 | Gilchrist | 424/604 |
| 5,509,889 A | * | 4/1996 | Kalb et al. | 600/30 |
| 5,558,629 A | * | 9/1996 | Baerveldt et al. | 604/8 |
| 5,800,339 A | * | 9/1998 | Salama | 600/29 |
| 5,860,916 A | * | 1/1999 | Pylant | 600/208 |
| 5,894,608 A | * | 4/1999 | Birbara | 4/144.3 |

(Continued)

FOREIGN PATENT DOCUMENTS

EP    0 258 057        3/1988
EP    0 258 057 A2     3/1988

(Continued)

OTHER PUBLICATIONS

European Search Report of Oct. 5, 2009.

(Continued)

*Primary Examiner* — Adam Marcetich

(74) *Attorney, Agent, or Firm* — Lisa E. Winsor, Esq.

(57) ABSTRACT

A valve assembly is provided which includes a housing having an inlet end and an outlet end and defining a fluid channel and a central chamber. A dissolvable valve member is positioned to obstruct flow through the channel within the chamber. The dissolvable valve member is formed of a material which is dissolvable at a predetermined rate upon contact with a preselected fluid. The preselected fluid is selected from the group consisting of blood, urine, saline and antimicrobial solutions. The dissolvable valve member can be formed from a fluid soluble glass or a starch based material.

10 Claims, 5 Drawing Sheets

(56) References Cited

U.S. PATENT DOCUMENTS

| | | | |
|---|---|---|---|
| 6,050,934 A | 4/2000 | Mikhail et al. | |
| 6,145,593 A | 11/2000 | Hennig | |
| 6,183,437 B1 | 2/2001 | Walker | |
| 6,245,228 B1 | 6/2001 | Kelada | |
| 6,551,838 B2 | 4/2003 | Santini, Jr. et al. | |
| 6,793,651 B1 | 9/2004 | Bennett et al. | |
| 7,226,441 B2 | 6/2007 | Kulessa | |
| 7,410,481 B1 * | 8/2008 | Mitts et al. | 604/544 |
| 2001/0037097 A1 * | 11/2001 | Cheng et al. | 604/329 |
| 2003/0171768 A1 | 9/2003 | McGhan | |
| 2003/0175853 A1 | 9/2003 | Clarke et al. | |
| 2003/0208183 A1 | 11/2003 | Whalen et al. | |
| 2005/0137570 A1 | 6/2005 | Jones et al. | |
| 2005/0148999 A1 * | 7/2005 | Beaufore et al. | 604/544 |
| 2005/0256447 A1 * | 11/2005 | Richardson et al. | 604/65 |
| 2005/0271698 A1 * | 12/2005 | Bucay-Couto et al. | 424/423 |
| 2006/0047247 A1 * | 3/2006 | Anders | 604/164.08 |
| 2006/0093528 A1 | 5/2006 | Banerjee et al. | |
| 2006/0142736 A1 * | 6/2006 | Hissink et al. | 604/540 |
| 2006/0212024 A1 | 9/2006 | Blake et al. | |
| 2007/0270734 A1 | 11/2007 | Crisp | |
| 2008/0051763 A1 | 2/2008 | Frojd | |
| 2008/0071250 A1 | 3/2008 | Crisp | |
| 2008/0188770 A1 * | 8/2008 | Hannon | 600/574 |
| 2009/0264840 A1 * | 10/2009 | Virginio | 604/319 |

FOREIGN PATENT DOCUMENTS

| | | |
|---|---|---|
| EP | 0 399 652 | 11/1990 |
| EP | 0 399 652 A1 | 11/1990 |
| GB | 1 534 219 | 11/1978 |
| GB | 1 534 219 A1 | 11/1978 |
| WO | 89/01793 A1 | 3/1989 |
| WO | WO 89/01793 | 3/1989 |
| WO | 2004/041122 A1 | 5/2004 |
| WO | WO 2004/041122 | 5/2004 |
| WO | 2006/020929 A1 | 2/2006 |
| WO | WO 2006/020929 | 2/2006 |
| WO | 2006/063593 A1 | 6/2006 |
| WO | WO 2006/063593 | 6/2006 |

OTHER PUBLICATIONS

European Search Report dated Oct. 5, 2009 for copending European Appln No. EP 09 16 3472.

* cited by examiner

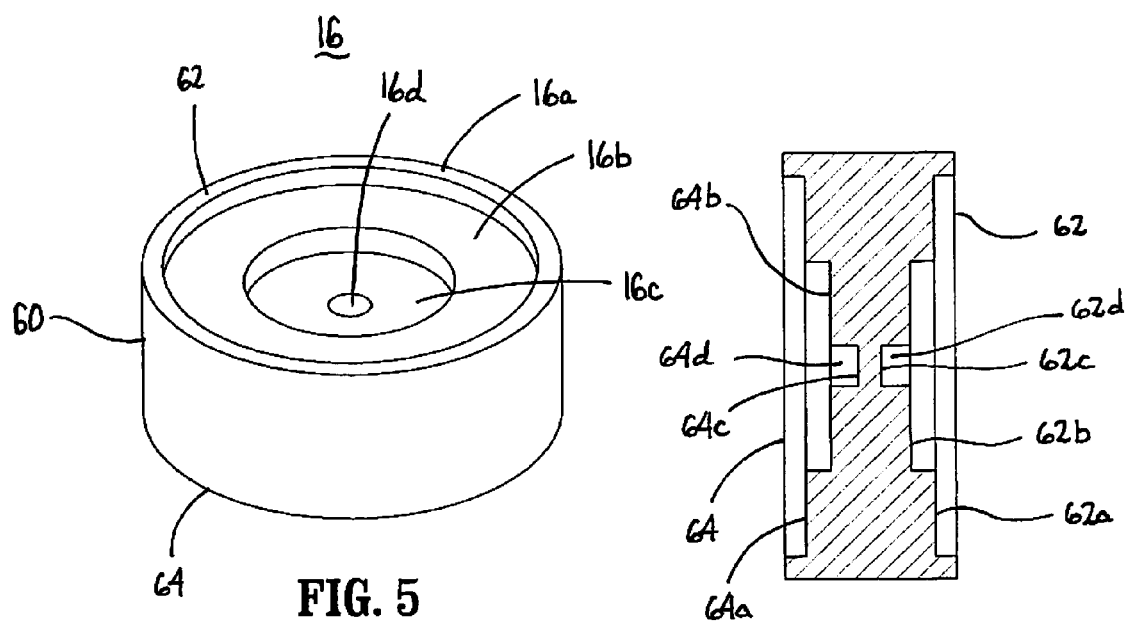
FIG. 5
FIG. 6
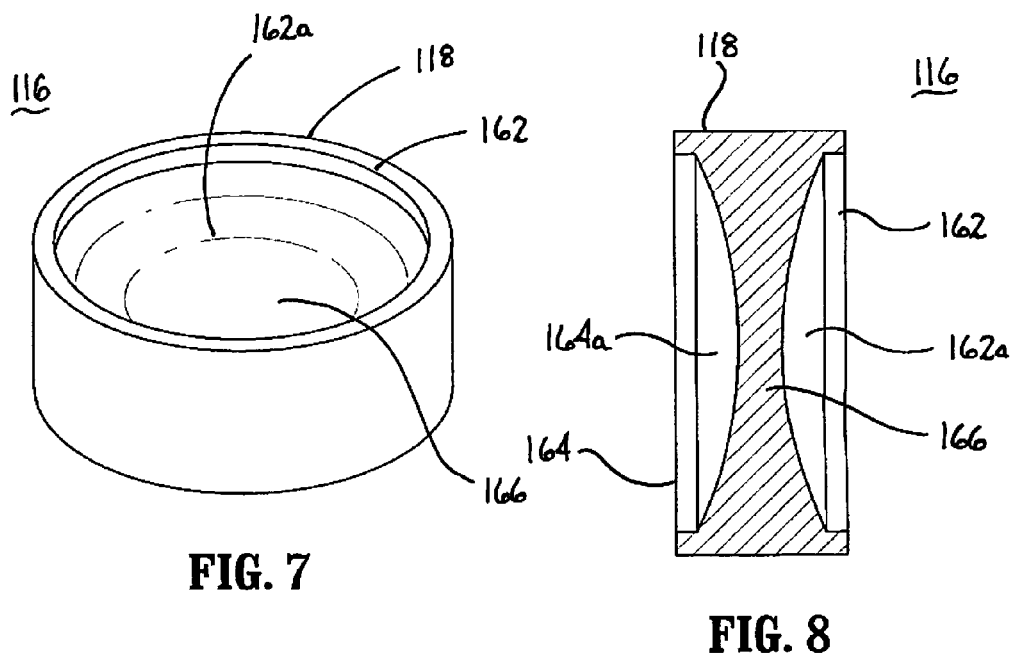
FIG. 7
FIG. 8

VALVE ASSEMBLY INCLUDING A DISSOLVABLE VALVE MEMBER

This application claims priority from U.S. provisional application Ser. No. 61/076,850, filed Jun. 30, 2008, the entirety of which is incorporated herein by reference.

BACKGROUND

1. Technical Field

The present disclosure relates to medical apparatus including a valve assembly having a dissolvable valve member and, more particularly, to a relief valve assembly having a dissolvable valve member for use with a urinary catheter.

2. Background of Related Art

Urinary catheters for draining fluid from a patient's bladder are well known in the art. Typically, urinary catheters include a flexible body which is dimensioned to be inserted through the urethra into the bladder. The distal end of the catheter includes an expandable bulb or balloon which can be expanded within the bladder, via a gas inlet valve and conduit, to retain the distal end of the catheter within the bladder. The flexible body further defines a drain lumen which allows fluid to drain from the bladder into a urine collection bag. The urinary catheter also includes a sampling port and an irrigation lumen which allows an irrigation fluid to be injected through the catheter into the bladder to irrigate the bladder. In addition to facilitating withdrawal of urine from the catheter for testing, the sampling port can also be used to inject an anti-microbial solution into the catheter to reduce the risk of infection to the patient.

When an irrigation fluid and/or an anti-microbial solution is injected into a catheter, medical personnel must clamp the catheter downstream of the injection site for a specified period of time to prevent the irrigation fluid and/or anti-microbial solution from immediately draining from the bladder and/or catheter. If the medical personnel fail to remove the clamp, fluid will back up in the bladder and result in discomfort and potential serious harm to the patient.

Accordingly, a continuing need exists in the medical arts for a device usable with a catheter which can retain an irrigation solution and/or anti-microbial solution within a catheter for a specified period of time and, thereafter, permit drainage of the catheter without intervention by medical personnel.

SUMMARY

A valve assembly is provided which includes a housing having an inlet end and an outlet end and defining a fluid channel and a central chamber. A dissolvable valve member is positioned to obstruct flow through the channel within the chamber. The dissolvable valve member is formed of a material which is dissolvable at a predetermined rate upon contact with a preselected fluid. The preselected fluid is selected from the group consisting of blood, urine, saline and antimicrobial solutions. The dissolvable valve member can be formed from a fluid soluble glass or a starch based material. Alternatively, the use of other dissolvable materials is envisioned. The housing can include an inlet housing portion and an outlet housing portion which are configured to be secured together to define the central chamber. The inlet end of the housing is adapted to releaseably engage a drain lumen of a medical device, e.g., urinary catheter. The outlet end of the housing is adapted to releasably engage a fluid conduit of a urine collection system. In one embodiment, the housing has at least one vent configured to vent air from within the valve assembly. The at least one vent can include an inlet vent and an outlet vent.

In one embodiment, the dissolvable valve member is formed from a thin dissolvable material. In another embodiment, the dissolvable valve member includes a substantially cylindrical body having an inlet side and an outlet side. At least one of the inlet side and the outlet side can define a spherical concavity. Alternatively, the cylindrical body can have substantially rectangular cross-section. In one embodiment, the cylindrical body defines a stepped cross-section, wherein a central portion of the body has a smaller width than an outer portion of the body. The body can define one or more throughbores.

A urinary catheter assembly is also provided which includes a catheter having a body defining a central drain lumen for positioning within a bladder of a patient having an outlet end defining a drain lumen outlet. A valve assembly includes a housing adapted to releasably engage the outlet end of the body of the catheter. The housing defines a fluid channel and a chamber. The valve assembly further includes a dissolvable valve member positioned to obstruct flow through the channel. The dissolvable valve member can be formed of a material which is dissolvable at a predetermined rate upon contact with a preselected fluid. The preselected fluid can be selected from the group consisting of blood, urine, saline and antimicrobial solutions. The dissolvable valve member can be formed from a fluid soluble glass or a starch based material. The housing can have at least one vent configured to vent air from within the valve assembly. Alternatively, the dissolvable valve member can be formed from a thin dissolvable material.

BRIEF DESCRIPTION OF THE DRAWINGS

Various embodiments of the presently disclosed valve assembly including a dissolvable valve member are disclosed herein with reference to the drawings, wherein:

FIG. 5 is a top perspective view of one embodiment of the dissolvable valve member of the presently disclosed valve assembly shown in FIG. 1;

FIG. 6 is a side cross-sectional view of the dissolvable valve member shown in FIG. 5;

FIG. 7 is a top perspective view of another embodiment of the dissolvable valve member of the presently disclosed dissolvable fluid relief valve assembly shown in FIG. 1;

FIG. 8 is a side cross-sectional view of the dissolvable valve member shown in FIG. 7;

DETAILED DESCRIPTION OF EMBODIMENTS

Figure 1:
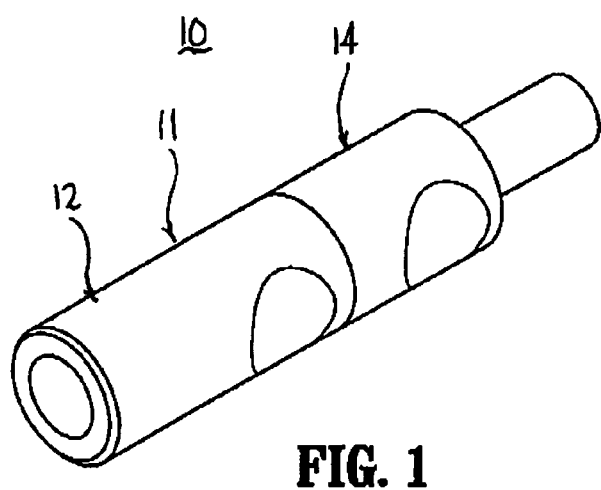
FIG. 1 is a side perspective view of one embodiment of the presently disclosed valve assembly.

Embodiments of the presently disclosed valve assembly including a dissolvable valve member will now be described in detail with reference to the drawings wherein like reference numerals designate identical or corresponding elements in each of the several views.

Figure 2:
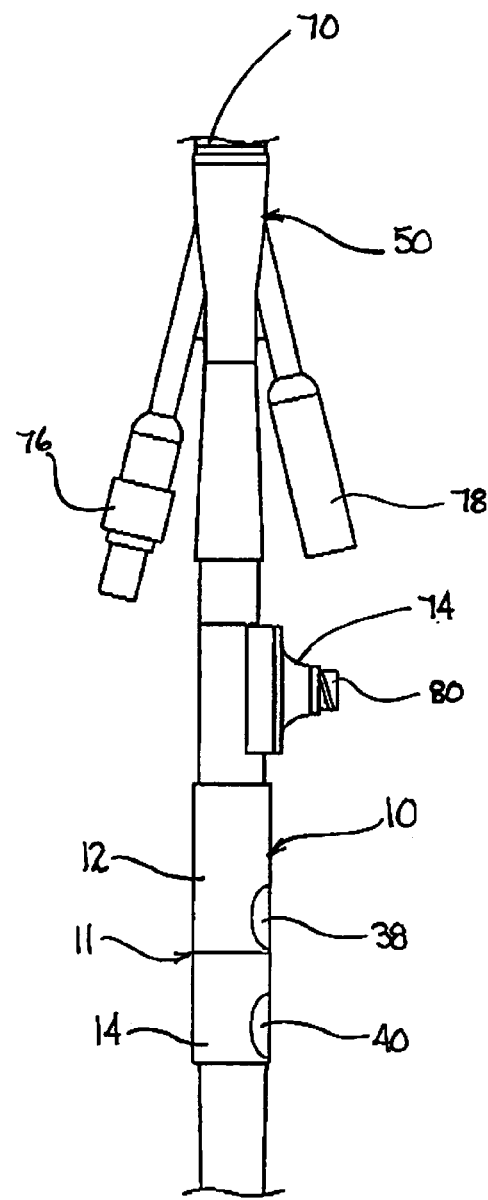
FIG. 2 is a side view of the valve assembly shown in FIG. 1 attached to a urinary catheter assembly.
Figure 3:
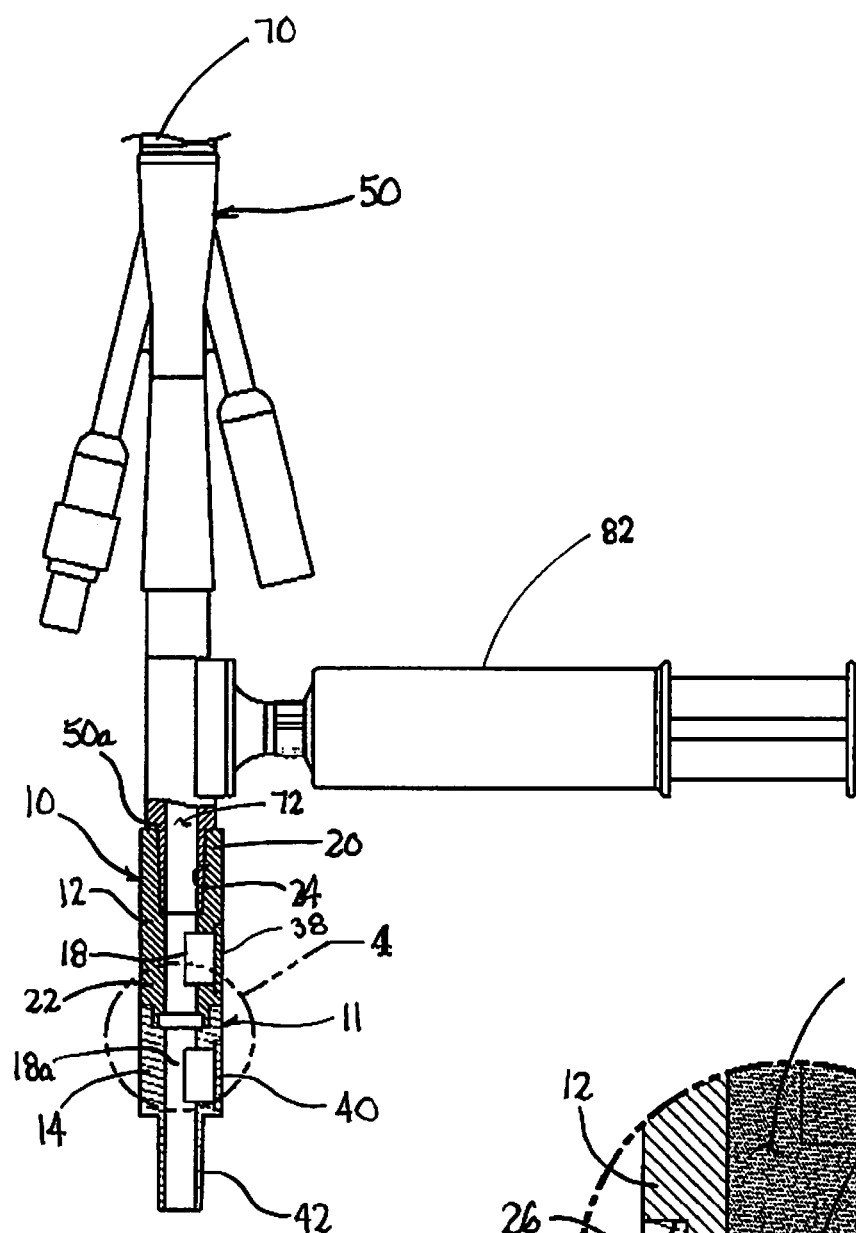
FIG. 3 is a side partial cross-sectional view of the valve assembly and urinary catheter assembly shown in FIG. 2 with a syringe assembly fastened to the urinary catheter assembly.
Figure 4:
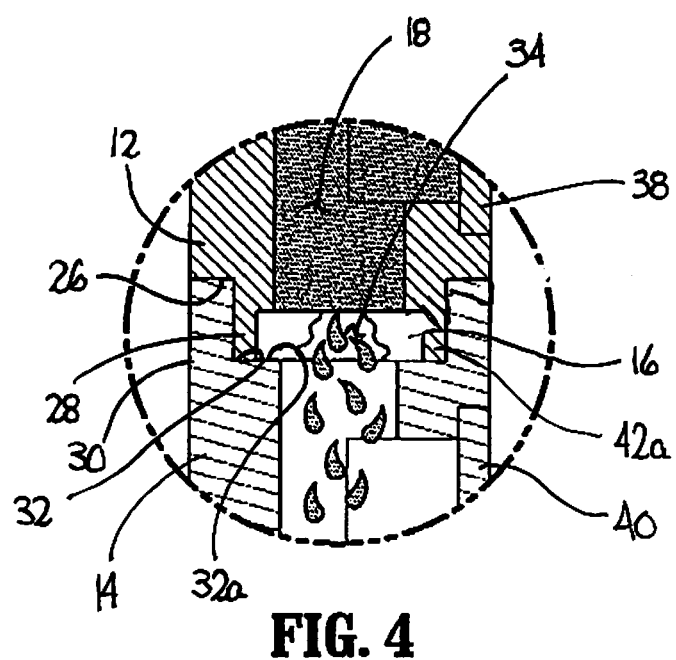
FIG. 4 is an enlarged view of the indicated area of detail shown in FIG. 3.

FIGS. 1-4 illustrate one embodiment of the presently disclosed valve assembly shown generally as 10. Valve assembly 10 includes a housing 11 which includes an inlet housing portion 12, and an outlet housing portion 14, and a dissolvable valve member 16 (FIG. 4). Inlet housing portion 12 is substantially tubular and defines a fluid channel 18 (FIG. 3). Inlet housing portion 12 includes an outlet end 22 and an inlet end 20. Inlet end 20 defines an inlet bore 24 which converges towards outlet end 22 and is dimensioned to releasably receive an outlet end 50a of a urinary catheter 50. Outlet end 22 of housing portion 12 defines an outer stepped portion 26 (FIG. 4) and an inner annular extension 28. Annular extension 28 defines a cylindrical chamber 34 (FIG. 4).

Outlet housing portion 14 defines a fluid channel 18a which is in fluid communication with fluid channel 18 of inlet housing portion 12. An inlet end 30 of outlet housing portion 14 has an inner stepped portion 32 which is dimensioned to receive annular extension 28 of inlet housing portion 12. Inner stepped portion 32 has a width which is greater than the width of annular extension 28 such that inner stepped portion 32 defines a shoulder 32a. Shoulder 32a and annular extension 28 together define cylindrical chamber 34. Chamber 34 is dimensioned to receive dissolvable valve member 16 as will be discussed in further detail below. Outlet end 22 of housing portion 12 is secured to inlet end 30 of outlet housing portion 14 such as by sonic welding, adhesives, screw threads, or the like, such that dissolvable valve member 16 is retained in chamber 34.

Inlet and outlet housing portions 12 and 14 can be formed from a clear or transparent material, e.g., transparent polymeric materials including polycarbonates. One such material which is commercially available is LEXAN®. A transparent material allows medical personnel to visually confirm that the valve assembly 10 is functioning properly, i.e., that the valve member 16 has dissolved in the specified period of time and that fluid is flowing through the valve assembly 10. It is envisioned that the valve member can include a contrasting color to improve visualization of the valve member.

Each of inlet and outlet housing portions 12 and 14 also includes a vent. More specifically, an upper vent 38 is supported on inlet housing portion 12 and a lower vent 40 is supported on housing portion 14. Vents 38 and 40 allow air from within catheter 50 and valve assembly 10 to be removed from fluid channels 18 and 18a. An outlet end 42 of housing portion 14 includes a thin walled extension 42a (FIG. 4) which is dimensioned to frictionally engage a collection tube (not shown) of a urine collection system (not shown).

FIGS. 5 and 6 illustrate one embodiment of the presently disclosed dissolvable valve member 16. Valve member 16 has a body 60 having an inlet side 62 and an outlet side 64. Each side includes an inwardly stepped configuration. More specifically, inlet side 62 includes a series of annular steps 62a, 62b and 62c and central blind bore 62d and outlet side 64 includes a series of annular steps 64a, 64b, 64c and a central blind bore 64d. The steps are configured such that the width of body 60 decreases towards a central axis of body 60. In one embodiment, valve body 60 is formed from a dissolvable material such as water soluble glass. Alternatively, other dissolvable materials of construction can be used to construct valve member 16 including starch based materials. The thickness and configuration of body 60 and the particular material of construction should be selected to provide the desired rate at which the valve member 16 dissolves.

Referring now to FIGS. 2 and 3, valve assembly 10 is particularly suited for use with a urinary catheter 50. Urinary catheter 50 includes an elongated flexible body 70 which is shown cutaway in FIGS. 2 and 3. A distal end (not shown) of body 70 is dimensioned to be inserted through the urethra and into the bladder. The distal end of body 70 includes an expandable member or balloon (not shown) for retaining the distal end of body 70 within the bladder.

Catheter assembly 50 includes a body defining a central drain lumen 72 (FIG. 3), a valved sampling port 74, a balloon supply port 76 and an irrigation lumen 78. Balloon supply port 76 provides an access port for supplying pressurized gas to the balloon (not shown). Irrigation lumen 78 communicates with a distal end (not shown) of body 70 to supply irrigation fluid to the bladder (not shown). Sampling port 74 includes a valved port which includes a connector 80 (FIG. 2) for releasably engaging a syringe fitting of a syringe assembly 82 (FIG. 3). Syringe assembly 82 can be used to inject fluid into or withdraw fluid from central drain lumen 72 of catheter assembly 50.

When inlet end 20 of inlet housing portion 12 of valve assembly 10 is releasably coupled with catheter assembly 50 and a distal end of catheter assembly 50 is inserted into a patient's bladder, an irrigation solution can be injected into the bladder by injecting the solution, e.g., saline, through the irrigation lumen 78 into the bladder. An anti-microbial solution, e.g., ethylene diamine tetraacetic acid ("EDTA"), can also be injected through supply port 76 into central drain lumen 72 of catheter assembly 50 to flush or lock the catheter. When an irrigation fluid and/or anti-microbial solution is injected into catheter assembly 50, the fluid will flow into central drain lumen 72 and enter channel 18 of inlet housing portion 12 of valve assembly 10. The dissolvable valve member 16 of valve assembly 10 is positioned between channel 18 of inlet housing portion 12 and channel 18a of outlet housing portion 14 to prevent or obstruct fluid from exiting drain lumen 72 until a predetermined period of time has elapsed. The dissolvable valve member 16 of valve assembly 10 allows medical personnel to lock and flush catheter assembly 50 without the need of a mechanical clamping device to ensure that drainage is reestablished without medical personnel intervention.

As discussed above, valve member 16 can be constructed from fluid soluble glass or, alternatively, from starch based materials, which can be designed to dissolve over time after exposure to blood, urine, saline or antimicrobial solutions such as EDTA. The soluble glass used may comprise phosphorus pent oxide as the principle glass forms together with any one or more glass-modifying non-toxic materials such as sodium oxide, potassium oxide, magnesium oxide and calcium oxide. Alternatively, other dissolvable materials may be used to form the valve member. Further, the dissolvable material, e.g., glass can be impregnated with a drug or anti-microbial which is released into the catheter or other medical device as the valve member dissolves. The materials noted above can be engineered to dissolve over specific time periods such as seconds, minutes and hours. Combinations of fluid temperature, valve surface area, geometry and material dissolution rate for both soluble glass and starch based material valve members allow for an infinite number of time ranges to be established in which the valve member would dissolve and fluid flow from the catheter would be reestablished.

Figure 9:
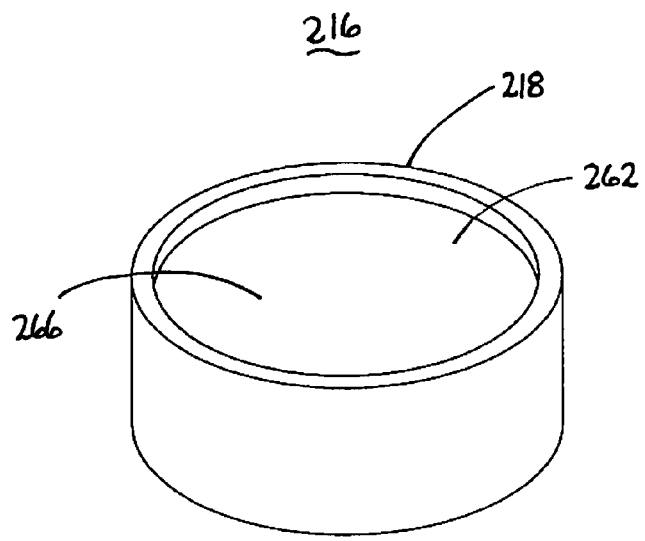
FIG. 9 is a top perspective view of another embodiment of the dissolvable valve member of the presently disclosed dissolvable fluid relief valve assembly shown in FIG. 1.
Figure 10:
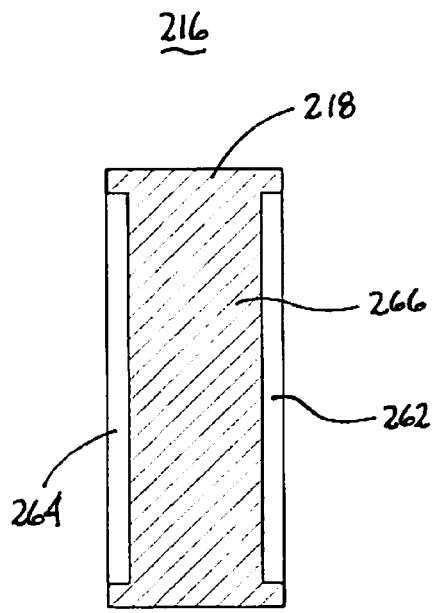
FIG. 10 is a side cross-sectional view of the dissolvable valve member shown in FIG. 9.
Figure 11:
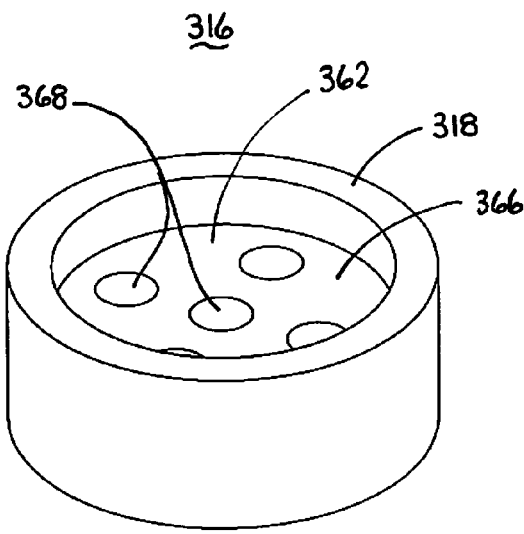
FIG. 11 is a top perspective view of another embodiment of the dissolvable valve member of the presently disclosed dissolvable fluid relief valve assembly shown in FIG. 1.
Figure 12:
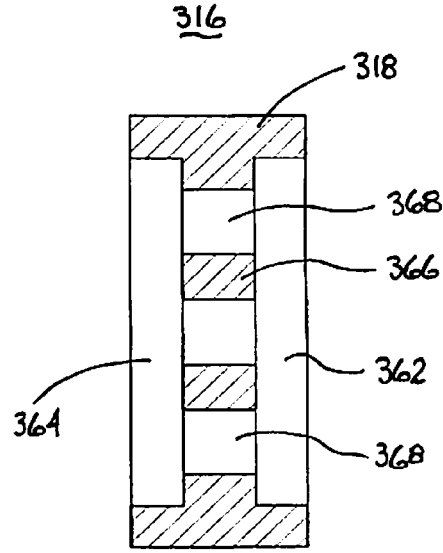
FIG. 12 is a side cross-sectional view of the dissolvable valve member shown in FIG. 11.

FIGS. 7-12 illustrate alternative embodiments of the dissolvable valve member 16. In FIGS. 7 and 8, valve member 116 has a substantially cylindrical body 118 which includes an inlet side 162 defining a substantially spherical concavity 162a and an outlet side 164 defining a substantially spherical concavity 164a. Concavities 162a and 164a are separated by a barrier 166. In FIGS. 9 and 10, valve member 216 includes a substantially cylindrical body 218 having a recessed inlet side 262, a recessed outlet side 264 and a barrier member 266 having a rectangular cross-section. In FIGS. 11 and 12, valve member 316 includes a substantially cylindrical body 318 having a recessed inlet side 362, a recessed outlet side 364 and a barrier member 366 having a rectangular cross-section and a plurality of through bores 368. Valve member 316 provides for a reduced flow rate through bores 368 of valve member 316. As the valve member 316 dissolves, the flow rate across the valve member will increase.

It is envisioned that a variety of valve member configurations can be used to achieve the advantages described. Only a few representative embodiments have been described herein. For example, the valve member need not be cylindrical but rather may assume a variety of different configurations, e.g., square, triangular, rectangular, etc.

Figure 14:
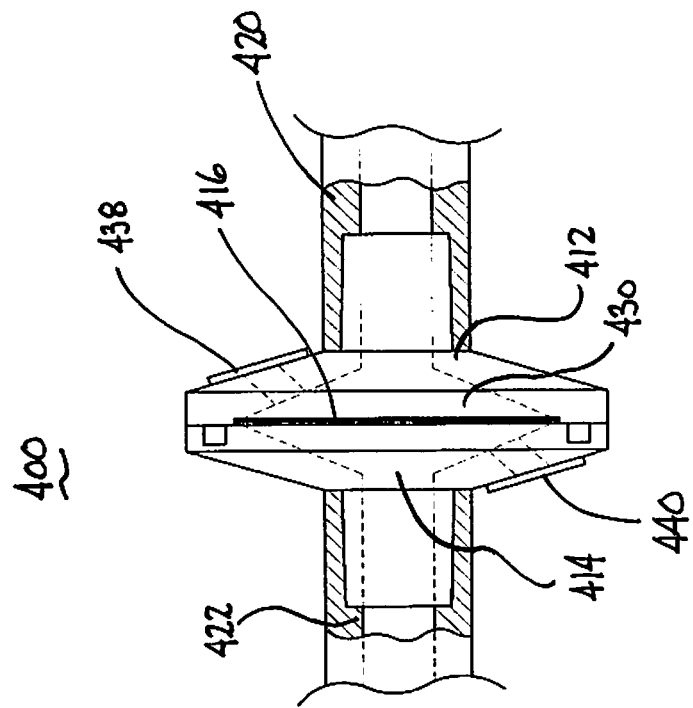
FIG. 14 is a side partial cross-sectional view of the valve assembly shown in FIG. 13.
Figure 13:
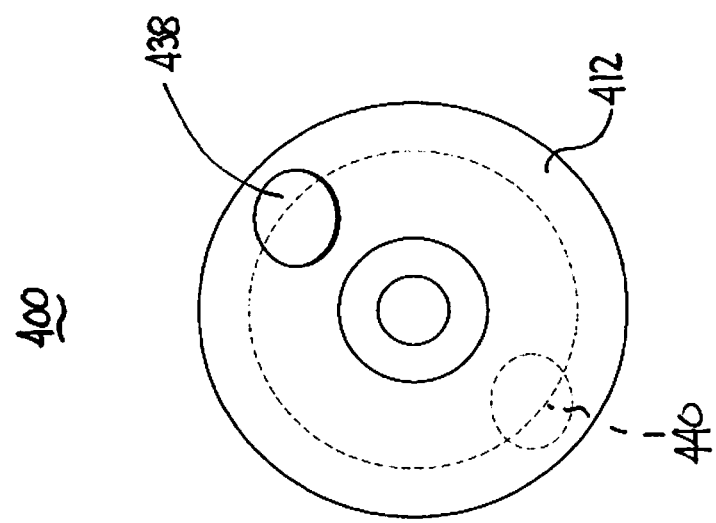
FIG. 13 is a top view of an alternative embodiment of the presently disclosed valve assembly including a dissolvable valve member.

FIGS. 13 and 14 illustrate an alternative embodiment of the presently disclosed valve assembly shown generally as 400. Valve assembly 400 includes an inlet housing portion 412, an outlet housing portion 414 and a valve member 416. Inlet housing portion 412 includes a vent 438 and outlet housing portion includes a vent 440. Inlet housing portion 412 includes an inlet conduit 420 which is adapted to be releasably connected to the drain tube of a catheter (not shown). Outlet housing portion 414 includes an outlet conduit 422 which is adapted to be releasably connected to a urine collection device. Inlet and outlet housing portions 412 and 414 define a valve chamber 430 which is divided by valve member 416. In one embodiment, valve member 416 is formed of a thin film starch based dissolvable material. Alternatively, other known dissolvable materials may be used.

In use, valve assembly 400 functions in a manner similar to valve assembly 10 as described above. More specifically, when a fluid, e.g., urine, blood, EDTA, etc., flows through inlet conduit 420 into valve chamber 430, the fluid engages valve member 416 causing valve member 416 to dissolve at a specified rate. When valve member 416 dissolves, fluid is able to flow through valve member 416 through outlet conduit 422.

It will be understood that various modifications may be made to the embodiments disclosed herein. For example, the valve assembly and/or valve member may assume a variety of configurations not shown herein, e.g., rectangular, square, oval, etc. Further, the valve assembly can be used in association with medical devices other than urinary catheters, including, for example, blood collection devices, IV administration sets, and abdominal drainage tubes. It is also envisioned that one or more dissolvable valve members can be used together. For example, three "five minute" dissolvable valve members may be used together to allow medical personnel to assess more easily the time remaining to re-establish flow. Therefore, the above description should not be construed as limiting, but merely as exemplifications of embodiments. Those skilled in the art will envision other modifications within the scope and spirit of the claims appended hereto.

What is claimed is:

1. A urinary catheter assembly comprising:
   a catheter having a body defining a central drain lumen for positioning within a bladder of a patient, the body having an outlet end defining a drain lumen outlet; and
   a valve assembly including a housing adapted to releasably engage the outlet end of the body of the catheter, the housing defining a fluid channel and a chamber, the valve assembly further including a dissolvable valve member positioned to prevent flow through the channel in its undissolved state, the dissolvable valve member being formed of a material which is dissolvable at a predetermined rate upon contact with a preselected fluid to automatically permit flow through the channel when a predetermined time has elapsed after contact with the preselected fluid.

2. The valve assembly according to claim 1, wherein the preselected fluid is selected from the group consisting of blood, urine, saline and antimicrobial solutions.

3. The valve assembly according to claim 1, wherein the dissolvable valve member is formed from a fluid soluble glass.

4. The valve assembly according to claim 1, wherein the housing has at least one vent configured to vent air from within the valve assembly.

5. The valve assembly according to claim 1, wherein the dissolvable valve member is formed from a thin dissolvable material.

6. The valve assembly according to claim 1, wherein the housing includes a shoulder defining a first end of the chamber.

7. The valve assembly according to claim 1, wherein the chamber is configured to receive the dissolvable valve.

8. The valve assembly according to claim 1, wherein at least a portion of the housing is substantially transparent.

9. The valve assembly according to claim 8, wherein the dissolvable valve member is a contrasting color to the preselected fluid.

10. The valve assembly according to claim 1, wherein the valve assembly has more than one dissolvable valve members disposed in series such that one dissolvable valve member transition to its undissolved state before the next dissolvable valve member comes into contact with the preselected fluid.

* * * * *